United States Patent
Tsai

(10) Patent No.: US 7,347,876 B2
(45) Date of Patent: Mar. 25, 2008

(54) METHOD FOR EXPANSION OF EPITHELIAL STEM CELLS

(76) Inventor: Ray Jui-Fang Tsai, 2F350 Section 4 Cheng Kung Road, Taipei (TW)

( * ) Notice: Subject to any disclaimer, the term of this patent is extended or adjusted under 35 U.S.C. 154(b) by 0 days.

(21) Appl. No.: 10/240,310

(22) PCT Filed: Apr. 25, 2001

(86) PCT No.: PCT/US01/13321

§ 371 (c)(1), (2), (4) Date: Dec. 13, 2002

(87) PCT Pub. No.: WO01/80760

PCT Pub. Date: Nov. 1, 2001

(65) Prior Publication Data

US 2003/0208266 A1 Nov. 6, 2003

(51) Int. Cl.
*A61F 2/02* (2006.01)
*A61F 2/14* (2006.01)
*C12N 5/08* (2006.01)

(52) U.S. Cl. .................. 623/23.76; 623/5.16; 623/915
(58) Field of Classification Search ............... 623/1.41, 623/5.16, 915–919, 23.76
See application file for complete search history.

(56) References Cited

U.S. PATENT DOCUMENTS

2002/0039788 A1* 4/2002 Isseroff et al. .............. 435/366

FOREIGN PATENT DOCUMENTS

JP 2001-161353 A * 6/2001
WO WO 98/37903 * 9/1998

OTHER PUBLICATIONS

U.S. Appl. No. 60/185,744, filed on Feb. 29, 2000.*
Wikipedia topic entitled "Stem cell", five pages, from http://en.wikipedia.org/wiki/Stem_Cell, accessed on Sep. 17, 2006.*
Schwab, "Composite amniotic membrane and corneal epithelial cell", Annu. meeting of the assoc. for research in Vis. & Ophth, May 14, 1999, vol. 40, No. 4, pp. s578.
Schwab, "Cultured coreneal epithelial for ocular surface disease", Transactions of the American Ophthalmological Society, 1999, vol. 97, pp. 891-986.
Tsai, "Reconstruction of damaged corneas by transplantation of autologous limbal epithelial cells", The New Eng. J. of Med., Jul. 13, 2000, Vol. 343, No. 2., pp. 86-93.
Grueterich, "Ex vivo expansion of limbal epithelial stem cells: amniotic membrane serving as a stem cell niche", Survey of Ophth., 2003, vol. 48, No. 6., pp. 631-646.
Tseng, "Amniotic Membrane Transplantation for Conjunctival Surface Reconstruction," Am. J. of Ophthalmology, vol. 124(6), pp. 765-774 (1997).

* cited by examiner

*Primary Examiner*—David H. Willse
(74) *Attorney, Agent, or Firm*—Panitch Schwarze Belisario & Nadel LLP

(57) ABSTRACT

Transplantation of epithelial stem cells, cultured ex vivo on specifically treated amniotic membrane, yields, with that amniotic membrane, a surgical graft having expanded epithelial stem cells. The method of creating this graft and the graft itself are simple and effective to reconstruct damaged tissue, a preferred example being corneal tissue. The source of the epithelial stem cells can be a very small explant from healthy autologous and allogeneic tissue biopsy. The amniotic membrane is treated such that its extracellular matrix is maintained, but its cells are killed.

10 Claims, No Drawings

METHOD FOR EXPANSION OF EPITHELIAL STEM CELLS

BACKGROUND OF THE INVENTION

Field of the Invention

This invention concerns epithelial stem cell and limbal stem cell deficiency and, more specifically, a method and graft for treating this problem of epithelial stem cell deficiency in, for example, the reconstruction of corneal surface.

PRIOR ART

With respect to the eye, the normal ocular surface is covered by corneal, limbal and conjunctival epithelia. Their distinct cellular phenotypes, together with a stable preocular tear film, maintain the ocular surface integrity. Severe limbal epithelial damage due to: chemical or thermal burns, Stevens-Johnson syndrome, ocular cicatricial pemphigoid, multiple surgeries and cryotherapies at the limbal region, contact lens wears and severe microbial infection can lead to limbal and epithelial stem cell deficiency. Limbal epithelial stem cell deficiency usually is manifested with conjuctivalization, vascularization, chronic inflammation and fibrous ingrowth onto the corneal surface and corneal opacification.

When limbal deficiency is unilateral or bilateral with asymmetrical involvement, autologous limbal tissue transplantation is suggested. One major concern of autologous limbal transplantation is that one or two limbal grafts, spanning the area of two to three clock hours of the limbus, have to be removed from the healthy fellow eye. There has been one report describing the potential complication in donor eyes. Experiments with rabbits also have shown that limbal deficiency can occur if the central corneal epithelium is removed subsequently from donor eyes, with prior limbal removal. Pellegrini et al., Lancet 1997; 349:990-993, reported the transplantation of corneal epithelial cell sheets expanded on 3T3 fibroblast feeder layer, for corneal surface reconstruction in two total limbal deficiency patients.

Recently, transplantation of amniotic membrane, as a substrate replacement, has been shown by Kim and Tseng, Cornea 1995; 15:473-84, to be effective in reconstructing the corneal surface in rabbits with total limbal epithelial stem cell deficiency.

SUMMARY OF THE INVENTION

In one example of this invention, limbal stem cells and epithelial cells from a small limbal biopsy, taken from a healthy eye, and in culture are expanded on a specially treated amniotic membrane. Employing such amniotic membrane as a substrate helps restore a non-inflamed limbal stroma and expand the limbal stem and epithelial stem cell populations. The resulting "product" cancan be transplanted, as a graft, to a denuded corneal surface, following superficial heretectomy to remove fibrovascular ingrowth. For damaged body areas other than the eye, a biopsy of healthy epithelial cells is from an adjacent tissue area, having the same or similar biologic/histologic characteristics, i.e. histocompatible with the damaged area.

DESCRIPTION OF A PREFERRED EMBODIMENT

Limbal biopsy is performed on a healthy eye, which can be a fellow eye of a patient or from another living individual. The eye lid is sterilized with Betadine®(povidone-iodine). Under sterile conditions, 1 to 2 mm$^2$ of the limbal tissue, containing epithelial cells and part of the corneal stroma tissue, is separated from the limbal margin and excised from superficial corneal stroma by lamellar keratectomy, with No. 66 Beaver® blade (Becton Dickinson, Franklin Lakes, NJ). The tissue is placed in a 35 mm dish containing 1.5 ml of culture medium, having per ml: DMEM (Dulbecco's modified Eagle's medium) and Ham's F12 (1:1 ratio), supplemented with 0.5% DMSO (dimethyl sulfoxide), 2 ug.mouse EGF (epidermal growth factor),1 µg bovine insulin, 0.1 µg cholera toxin and 5% fetal bovine serum and it is sent immediately to the laboratory for culture in a sterile, laminar flow hood.

Amniotic membrane (obtained from Bio Tissue, Miami, Fla.) is used as a, culture system and is obtained, processed and preserved as reported by Tseng SCG in Am. J. Opthalmol 1997; 124:765-774 and Tseng U.S. Pat. No. 6,152,142, the teaching of which is incorporated herein. The amniotic membrane, with basement membrane side up, is affixed smoothly onto a culture plate and placed at 37° C. under 5% $CO_2$ and 95% air, in a humidified incubator overnight before use. Limbal explant culture is performed as previously described (Tsai and Tseng, Invest Opthalmol Vis Sci 1988; 29:97-108; and Tsai, et al., Invest Opthalmol Vis Sci 1994; 35:3865-2875), with some modifications. Instead of transfer onto a plastic substrate, as taught in these references, the limbal explant with the epithelial stem cells is planted/transferred onto the basement membrane side of the amniotic membrane in a 35 mm dish containing 1 ml of the above described culture medium. The medium is changed every two days, and the culture is maintained for 2 to 3 weeks, by which time the epithelial stem cells have grown and spread to form a cell layer covering an area of about 2 to 3 cm in diameter, for corneal surface reconstruction. For other tissue repair, more or less epithelial stem cell layer area can be employed, as needed.

Continuing with the example of corneal repair, following periotomy at the limbus, the perilimbal subconjunctival scar and inflamed tissues are removed to the bare sclera. The fibrovascular tissue of cornea is removed by lamellar keratectomy, with No. 57 and 66 Beaver blades, in a manner similar to that described for allograft limbal transplantation (Tsai and Tseng Cornea 1994; 13:389-400). For those patients with partial to total limbal corneal damage, but with normal central cornea, the cultivated limbal epithelial stem cells with the amniotic membrane is used as a sectorial limbal corneal graft, or a limbal equivalent, fashioned according to the size of the recipient eye, and transplanted to the corresponding recipient limbal area (from 90° to 360°). For those patients with total limbal and corneal surface damage, the novel graft is used as a whole lamellar corneal tissue, or a limbal corneal equivalent, and transplanted as lamellar keratoplasty to cover the entire area.

A properly sized, cultured, epithelial stem cell sheet on the treated amniotic membrane substrate is affixed to cover the entire defect with the epithelial side up, which can be readily identified by fluorescent staining or by the presence of loosely attached original explant. The graft then is secured to the damaged site. For a damaged cornea, securing can be by interrupted 10-0 nylon sutures on the corneal side, and interrupted 8-0 Vicryl® sutures to the surrounding conjunctival edge with episcleral anchorage. During the entire procedure, the cultured epithelium stem cell layer is protected from exposure, drying and abrasion by a coating of sodium hyaluronic (hyaluronate) acid Healon® (Pharmacia & Upjohn AB, Uppsala, Sweden). The original explant tissue can be removed from the amniotic membrane at the end of surgery. If this graft is over the cornea, the eye is pressure patched overnight, a therapeutic contact lens is placed the next day, for one week; and topical prednisolone acetate 1% solution is administered four times a day for the first week, twice a day for the next two weeks, and followed by 0.1% fluorometholone twice a day for 2 to 3 months, depending on the severity of conjunctival inflammation around the surgical area.

As stated hereinabove, the explant is cultured onto the basement membrane side of the specially treated amniotic membrane. After 2 to 3 weeks, the epithelial stem cells grow to form a sheet approximately 2 to 3 cm$^2$ in size on the amniotic membrane. Flat-mount preparation shows the epithelial stem cell layer is negative to PAS and Alcian blue staining; and the bare amniotic membrane is stained purple. Histological examinations show that epithelial sheet is composed of 4 to 5 stem cell layers at the margin of the sheet and from 1 to 4 cell layers in the area between the margin and original explant tissue. Ultrastructural examinations reveal the presence of loose and wide intercellular spaces and basement membrane structure, with focal condensation of electron-dense ground substance at the basal cell-amniotic membrane junction.

With respect to an embodiment of the invention specific to the treatment of eyes, a mean (±SD) follow-up period of 14.8±1.9 months shows varying degrees of visual improvement based on the Snellen visual acuity scale. All eyes show complete re-epithelialization in 2 to 4 days with a mean (±SD) period of 2.7±0.8 days. The reconstructed corneal surfaces show reduced inflammation and regression of vascularization within 1 to 2 weeks. One month after operation, the corneal clarity is improved and the surface smooth and wettable.

Depending on the area of limbal corneal damage, the cultured epithelial stem cells, expanded on a specially prepared amniotic membrane substrate, can be used as a limbal equivalent or a limbal-corneal equivalent.

Limbal deficiency of the donor eye, due to removal of a relatively large piece of limbus for transplantation, has been reported in rabbits. Thus, the new method and resulting graft of this invention substantially reduces the potential complications to the donor eye, since only a small piece of limbus is removed. Moreover, this method also can be performed in eyes with bilateral limbal deficiency with asymmetrical involvement. Ex vivo expansion of autologous epithelial stem cells on specially pre-treated amniotic membrane provides sufficient epithelial stem cells for transplantation in 2 to 3 weeks. For patients with bilateral total limbal deficiency, limbus from compatible sources, another living, related individual, should be considered for use according to this invention.

The use of uniquely pre-treated amniotic membrane based autologous epithelial stem cells for transplantation also provides all the beneficial effects inherent in amniotic membrane transplantation, including facilitating epithelization, reducing inflammation and scarring, and substrate replacement when the underlying stromal tissue is destroyed. Most importantly, amniotic membrane, pre-treated according to Tseng, provides a natural substrate for epithelial stem cells to be preserved and expand, forming the autologous cell mass necessary for corneal reconstruction. Moreover, because only the autologous cells are transplanted, immunosuppression is not required after transplantation. For allogeneic stem cells transplanted in this manner, the rejection rate may be lessened, since only epithelial stem cells, without other cell types, are transplanted.

As stated hereinabove, this unique graft and the method of its forming, by use of specially treated amniotic membrane, upon which epithelial stem cells from an explant are expanded, have uses beyond that of eye surgery, for example, repair of burned skin areas; especially when the donor site of the explant needs to be small. Likewise, the biopsy, from which the small explant is obtained, need not be of limbal tissue. The explant is to have healthy tissue, contain epithelial stem cells and be histocompatible with the recipient site for the graft. If the biopsy cannot be from the same body part as the recipient site, a corresponding similar body part can be chosen for the explant; just as in the preferred example of a damaged eye being the recipient site and the other eye—the healthy eye—providing donor explant.

It is believed that a unique and inventive surgical graft and method of its creation have been disclosed sufficiently for those skilled in the art to practice the invention without significant experimentation, as well as develop modifications which lie within the spirit and scope of the invention as defined by its claims.

What is claimed is:

1. A surgical graft to be applied to a recipient site to restore the recipient site, said graft comprising:
   an isolated amniotic membrane comprising amniotic cells and an extracellular matrix having integrity; and
   healthy epithelial stem cells expanded by culturing on said amniotic membrane, said healthy epithelial stem cells originating from tissue treated in a culture medium which then are transferred to said amniotic membrane,
   whereby said graft restores the recipient site by transplanting to said site only said healthy epithelial stem cells cultured on said amniotic membrane.

2. The surgical graft according to claim 1 in which, said amniotic membrane has a basement membrane side; and said healthy epithelial stem cells are expanded on said basement membrane side.

3. The surgical graft according to claim 1 in which, limbal tissue, from a limbal biopsy performed on a healthy eye, is the source of said healthy epithelial stem cells.

4. The surgical graft according to claim 1 in which, said amniotic membrane has a basement membrane side; and
   said healthy epithelial stem cells are cultured ex vivo on said basement membrane side of said amniotic membrane.

5. The surgical graft as claimed in claim 1 in which,
   the source of said healthy epithelial stem cells is tissue from a biopsy taken from a healthy site corresponding biologically and histocompatible to the recipient site.

6. A method for creating a surgical graft for restoring a damaged recipient site, said method comprising the steps of:
   a) placing, as an explant, a biopsy containing healthy epithelial stem cells onto an isolated amniotic membrane, said amniotic membrane comprising amniotic cells and an extracellular matrix having integrity, said healthy epithelial stem cells originating from tissue treated in a culture medium which then are transferred to said amniotic membrane; and
   b) enabling said healthy epithelial stem cells to expand on said amniotic membrane, whereby, said damaged recipient site is restored by transplanting to said site only said healthy epithelial stem cells cultured on said amniotic membrane.

7. The method according to claim 6 in which, said amniotic membrane has a basement membrane side; and
said step of placing includes mounting said explant onto said basement membrane side.

8. The method according to claim 7 in which, said mounting causing said expanded healthy epithelial stem cells to be positioned face up with reference to the damaged recipient site.

9. The method according to claim 6 in which, said step of enabling includes
culturing said amniotic membrane, with its explant, for a duration sufficient for said healthy epithelial stem cells to have expanded to an area of about 2 to 3 cm in diameter.

10. The method according to claim 6 including
removing said explant from said amniotic membrane after securing said graft surgically to the recipient site.

* * * * *